(12) United States Patent
Maerz et al.

(10) Patent No.: US 10,280,128 B2
(45) Date of Patent: May 7, 2019

(54) AROMATICS ALKYLATION PROCESS

(71) Applicant: BADGER LICENSING LLC, Boston, MA (US)

(72) Inventors: Brian Maerz, Chelmsford, MA (US); Douglas Hubbell, Sudbury, MA (US); Maruti Bhandarkar, Kingwood, TX (US); Vijay Nanda, Houston, TX (US)

(73) Assignee: BADGER LICENSING LLC, Boston, MA (US)

( * ) Notice: Subject to any disclaimer, the term of this patent is extended or adjusted under 35 U.S.C. 154(b) by 708 days.

(21) Appl. No.: 14/416,193

(22) PCT Filed: Jul. 25, 2013

(86) PCT No.: PCT/US2013/052056
§ 371 (c)(1),
(2) Date: Jan. 21, 2015

(87) PCT Pub. No.: WO2014/018752
PCT Pub. Date: Jan. 30, 2014

(65) Prior Publication Data
US 2015/0197466 A1 Jul. 16, 2015

Related U.S. Application Data

(60) Provisional application No. 61/675,949, filed on Jul. 26, 2012.

(51) Int. Cl.
*C07C 2/66* (2006.01)
*C07C 7/13* (2006.01)
(Continued)

(52) U.S. Cl.
CPC ............ *C07C 7/13* (2013.01); *B01J 20/08* (2013.01); *B01J 20/18* (2013.01);
(Continued)

(58) Field of Classification Search
None
See application file for complete search history.

(56) References Cited

U.S. PATENT DOCUMENTS 4,273,621 A 6/1981 Fornoff
4,421,532 A 12/1983 Sacchetti
(Continued)

OTHER PUBLICATIONS

International Search Report and Written Opinion issued in the corresponding PCT/US2013/052056 dated Nov. 8, 2013.

*Primary Examiner* — In Suk C Bullock
*Assistant Examiner* — Ali Z Fadhel
(74) *Attorney, Agent, or Firm* — Roberts Mlotkowski Safran Cole & Calderon P.C.

(57) ABSTRACT

In a process for alkylating an aromatic hydrocarbon feedstock with an olefin feedstock, at least one of the aromatic hydrocarbon and olefin feedstocks is passed through a pretreatment unit containing an adsorbent such that the adsorbent removes impurities contained by the feedstock. Passage of the at least one feedstock through the pretreatment unit is then terminated and a heated inert gas is passed through the pretreatment unit such that the inert gas desorbs impurities from the adsorbent to produce an inert gas effluent stream containing the desorbed impurities. A condensable fluid is added to at least part of the inert gas effluent stream such that at least a portion of the impurities contained therein condense with said fluid to leave a purified inert gas stream, which is recycled to the pretreatment unit.

13 Claims, 1 Drawing Sheet

(51) Int. Cl.
  *B01D 15/08* (2006.01)
  *B01J 20/08* (2006.01)
  *B01J 20/18* (2006.01)
  *B01J 20/28* (2006.01)
  *B01J 20/34* (2006.01)
  *C07C 15/04* (2006.01)

(52) U.S. Cl.
  CPC ....... *B01J 20/28052* (2013.01); *B01J 20/345* (2013.01); *B01J 20/3408* (2013.01); *C07C 2/66* (2013.01); *B01D 15/08* (2013.01); *C07C 2529/06* (2013.01)

(56) References Cited

U.S. PATENT DOCUMENTS

| | | | |
|---|---|---|---|
| 4,487,614 A | | 12/1984 | Yon |
| 4,494,967 A | | 1/1985 | Barth |
| 5,152,812 A | * | 10/1992 | Kovach ............... B01D 5/0039 95/141 |
| 5,334,795 A | | 8/1994 | Chu et al. |
| 7,777,086 B2 | | 8/2010 | Hwang et al. |
| 7,868,215 B2 | | 1/2011 | Dandekar et al. |
| 2004/0242404 A1 | | 12/2004 | Hwang et al. |
| 2005/0143612 A1 | * | 6/2005 | Hwang .................... C07C 2/66 585/449 |
| 2008/0029437 A1 | * | 2/2008 | Umansky ............ B01J 20/3408 208/238 |
| 2008/0139857 A1 | | 6/2008 | Henn et al. |
| 2012/0090465 A1 | | 4/2012 | Winter |

\* cited by examiner

AROMATICS ALKYLATION PROCESS

CROSS-REFERENCE TO RELATED APPLICATIONS

The present application is a U.S. National Phase of PCT/US2013/05256 filed on Jul. 25, 2013 claiming priority to U.S. provisional application No. 61/675,949 filed Jul. 26, 2012. The disclosure of the PCT Application is hereby incorporated by reference into the present Application.

FIELD

This invention relates to an aromatics alkylation process.

BACKGROUND

In aromatics alkylation, an aromatic compound, such as benzene, is contacted with an olefin, such as ethylene or propylene, in the presence of a catalyst to produce an alkylated aromatic compound, such as ethylbenzene or cumene. On a commercial scale, it is generally necessary to pass the olefin and aromatic feeds through one or more pretreatment units to reduce the level of certain impurities which are believed to be adsorbed by the process catalysts, reducing their activity. Typically, such pretreatment units include one or more adsorbent beds, conveniently composed of a molecular sieve or activated alumina, which selectively adsorb the harmful impurities in the feed. Each adsorbent bed is cycled between an adsorption cycle in which the bed is used to remove harmful impurities from one or more alkylation feeds, and a reactivation cycle, in which a hot inert gas, such as nitrogen, is passed through the bed to desorb the harmful impurities contained by the bed. Since a single pass of the inert gas through the adsorbent bed is uneconomic, many plants use a gas recirculation system to reduce inert gas usage.

Such gas recirculation systems typically include a compressor, heater, cooler, chiller, and gas/liquid separator Implicit in the design of such systems is the assumption that condensable compounds will be present in the inert gas exiting the pretreatment unit, and that at least a portion of the harmful impurities desorbed during each pass through the pretreatment unit will exit the system in the liquid collected in the gas/liquid separator. The inert gas from the separator is compressed, heated, and returned to the pretreatment unit. Typically only a small portion of the inert gas circulation is purged, so it would be inefficient to reject harmful impurities solely in the purge stream. One problem with this known process is that the harmful impurities may continue to desorb long after all of the condensable compounds have desorbed and condensed As a result, the recycled inert gas may still contain significant quantities of harmful impurities and so may be incapable of effecting complete reactivation of the adsorbent bed. According to the invention, this problem can be ameliorated or overcome, by adding a condensable fluid to the inert gas effluent from the adsorbent beds during reactivation cycles. The condensable fluid provides a medium in which the harmful impurities can be removed in the gas/liquid separator, so that the inert gas recycled to the absorbent bed has a much lower level of impurity than is obtained without the addition of the condensable liquid.

SUMMARY

In one aspect, the invention resides in a process for alkylating an aromatic hydrocarbon with an olefin, the process comprising:

(a) passing a feedstock selected from the aromatic hydrocarbon and the olefin through a pretreatment unit containing an adsorbent such that the adsorbent removes impurities contained by the feedstock;

(b) terminating passage of said feedstock through the pretreatment unit;

(c) passing a heated inert gas through the pretreatment unit such that the inert gas desorbs impurities from the adsorbent to produce an inert gas effluent stream containing the desorbed impurities;

(d) adding a condensable fluid to at least part of the inert gas effluent stream such that at least a portion of the impurities contained therein condense with said fluid to leave a purified inert gas stream; and (e) recycling the purified inert gas stream to (c).

Generally, the passing (a) is conducted at a first temperature and the inert gas is heated in (c) to a second temperature at least 50° C. higher than the first temperature. Typically, when the feedstock is said aromatic hydrocarbon, the first temperature is from about 100° C. to 170° C., preferably from about 110° C. to 130° C. When the feedstock is said olefin, the first temperature is from about 20° C. to 100° C., preferably from about 40° C. to 70° C.

In one embodiment, the inert gas comprises nitrogen and the condensable fluid is selected from ethylbenzene plant residue, cumene plant residue, ethylbenzene, cumene, benzene, water and mixtures thereof.

Typically, the aromatic hydrocarbon comprises benzene and the olefin comprises ethylene or propylene.

Conveniently, the impurities in said at least one feedstock are selected from inorganic or organic compounds containing nitrogen, sulfur, phosphorus, or oxygen atoms.

Conveniently, the inert gas effluent is passed through a liquid-cooled chiller to a gas/liquid separator where said impurities are removed with the condensed fluid. In one embodiment, the condensable fluid is added to the inert gas stream upstream of the chiller. In another embodiment, the condensable fluid is added to the inert gas stream downstream of the chiller but upstream of the gas/liquid separator.

DETAILED DESCRIPTION OF THE EMBODIMENTS

Figure 1A:
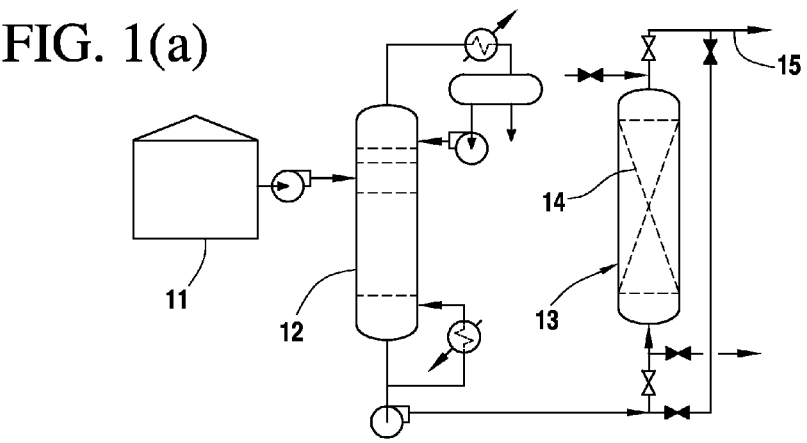
FIGS. 1 (a) and (b) are schematic diagrams of a pretreatment unit for removing impurities from an aromatic hydrocarbon feedstock to an aromatics alkylation process.

Described herein is an aromatics alkylation process in which one or both of the olefin and aromatic hydrocarbon feedstocks are pretreated to remove harmful impurities by passage of the feedstock through at least one pretreatment unit containing an adsorbent effective to selectively adsorb impurities from the feedstock. The adsorbed impurities are subsequently removed from the adsorbent by reactivation with a heated inert gas and a condensable fluid is then added to the inert gas to assist in separation of the desorbed impurities from the inert gas and produce a purified inert gas stream. The purified inert gas stream is then reheated and recycled to the reactivation process.

The pretreatment process described can be used with any aromatic hydrocarbon or olefinic feedstock to an aromatics alkylation process, but in general is intended for use in the purification of the benzene and/or ethylene feeds to a zeolite-catalyzed process for producing ethylbenzene or in the purification of the benzene and/or propylene feeds to a zeolite-catalyzed process for producing cumene. Examples of such processes are disclosed in, for example, U.S. Pat. Nos. 5,334,795 and 7,868,215, the entire contents of which are incorporated herein by reference.

Where both of the olefin and aromatic hydrocarbon feedstocks are pretreated, separate pretreatment units are employed for each feedstock.

The adsorbents employed in the or each pretreatment unit will depend on whether the feedstock to be treated is an olefin or an aromatic hydrocarbon and the nature of the impurities being targeted. Typical impurities that can be prejudicial to the zeolite alkylaton catalyst include inorganic and organic compounds containing nitrogen, sulfur, phosphorus, or oxygen atoms. For example, particularly deleterious impurities found in commercial benzene feedstocks include morpholine, N-formylmorpholine, n-methylpyrrolidone, diethylene glycol, monoethanolamine, diethanolamine, and para-dioxane, whereas targeted impurities in ethylene and propylene feeds include ammonia, dimethylformamide, dimethylamine, acetonitrile, methanol, and ethylene glycol. Typical aromatic and olefinic feedstocks may contain from 0.05 to 2 ppm by weight of these impurities. Suitable adsorbents for removing these impurities are capable of reactivation and include activated alumina and molecular sieves, such as zeolite 13x.

A single bed of adsorbent can be provided in the or each pretreatment unit or multiple stacked beds of the same or different adsorbents can be arranged in the pretreatment unit(s). Similarly, where a plurality of pretreatment units is arranged in series, the same or different adsorbents can be provided in the different units.

Generally, the conditions in the or each pretreatment unit are selected such that the adsorption of the targeted impurities is maximized without resulting in undesirable side reactions with the feedstock. Thus, when the feedstock is an aromatic hydrocarbon, such as benzene, the treatment temperature is from about 100° C. to 170° C., preferably from about 110° C. to 130° C. When the feedstock is an olefin, such as ethylene or propylene, the treatment temperature is from about 20° C. to 100° C., preferably from about 40° C. to 70° C. Under such conditions and using the adsorbents discussed above the impurity level in the feedstock can be reduced to levels of about 0.01 to 0.1 ppm by weight.

When the adsorbent in any given pretreatment unit is spent, the unit is bypassed and typically the feedstock is routed to a different unit. In the case of a benzene feedstock, when the adsorbent is spent, the liquid contents of the pretreatment unit are pressured out to the distillation train of the associated aromatics alkylation system. In the case of a spent ethylene adsorbent, the contents of the pretreatment unit are depressured to a flare. When the contents of the pretreatment unit have been removed, reactivation of the spent adsorbent is initiated by passing a heated inert gas, such as nitrogen, through the adsorbent. The gas temperature is adjusted such that the temperature of the adsorbent bed increases by 20-30° C. per hour until a target maximum bed temperature is achieved, normally at least 50° C. higher, such as about 50° C. to about 200° C. higher, than the temperature employed during the adsorption step.

The hot inert gas strips the impurities from the adsorbent and the desorbed impurities are removed from the pretreatment unit with the inert gas. After exiting the pretreatment unit, the inert gas containing the impurities is cooled and fed to a gas/liquid separator where impurities are removed before the inert gas is recycled to the pretreatment unit.

When the outflow from the pretreatment unit no longer contains condensable impurities (i.e., the rate of accumulation of liquid in the gas/liquid separator drops to near zero) a condensable fluid is added to the inert gas upstream of the gas/liquid separator so as to assist in further condensation of impurities from the inert gas stream. Suitable condensable fluids are selected from ethylbenzene plant residue, cumene plant residue, ethylbenzene, cumene, benzene, water and mixtures thereof, with water being preferred.

Figure 1B:
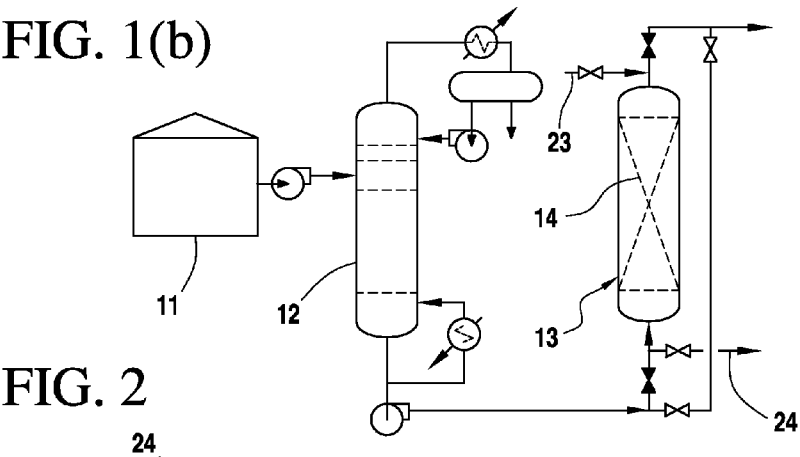
Figure 2:
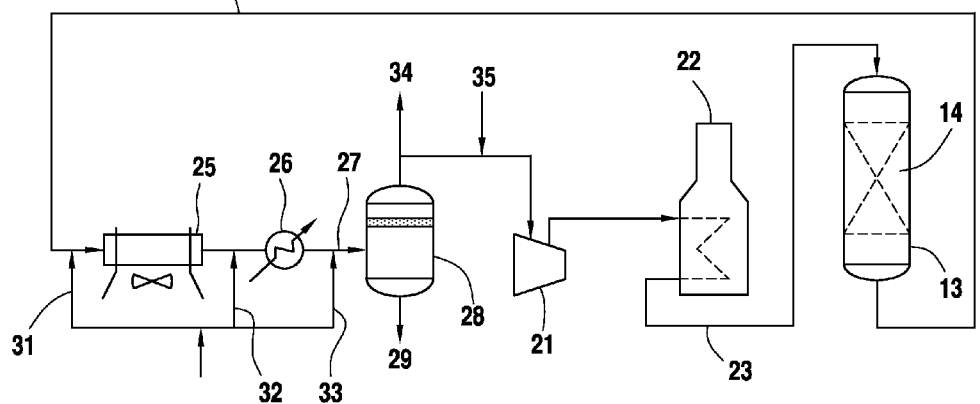
FIG. 2 is a flow diagram of the gas recirculation system of the pretreatment unit shown in FIG. 1.

The invention will now be more particularly described with reference to the accompanying drawings, in which FIG. 1 illustrates a pretreatment unit for removing impurities from a benzene feedstock, whereas FIG. 2 illustrates the inert gas recirculation system associated with the pretreatment unit of FIG. 1. The pretreatment unit shown in FIG. 1 cycles between an adsorption cycle, shown in FIG. 1 (*a*), in which the unit adsorbs impurities from a benzene hydrocarbon feedstock, and a reactivation cycle shown in FIG. 1 (*b*), in which impurities adsorbed during the previous adsorption cycle are removed.

In particular, as shown in FIG. 1 (*a*), during each adsorption cycle, fresh benzene, containing impurities, is pumped from a feed tank 11 via a drying column 12 to a pretreatment unit 13. The unit 13 contains a bed 14 of an adsorbent, which is maintained at a first temperature of about 110 to 130° C. during each adsorption cycle. The benzene feed is pumped into one end of the pretreatment unit 13 and flows through the adsorbent bed 14, where at least part of the impurities are removed, before a treated benzene stream exits the opposite end of the unit 13 through line 15.

After a predetermined amount of impurities have been taken up by the bed 14, the adsorbent is considered spent and the supply of fresh benzene to the unit 11 is by-passed and fed to another pretreatment unit (not shown). Then, after the bed 14 is substantially purged of benzene, a reactivation cycle is initiated. As shown in FIGS. 1 (*b*) and 2, during each reactivation cycle, an inert gas is compressed in a compressor 21 and then passed through a heater 22 before being fed by line 23 to the pretreatment unit 13. The heated inert gas flows through the adsorbent bed 14 countercurrent to the flow of liquid benzene through the bed during each adsorption cycle, and increases the temperature of the bed to a second temperature which is generally at least 50° C. higher, such as from 50 to 200° C. higher, than the first temperature. In one embodiment, the second temperature is about 200 to 300° C. Under these conditions, the inert gas desorbs the impurities removed from the benzene during the previous adsorption cycle so that a hot impurity-containing inert gas stream exits he pretreatment unit 13 through line 24. The hot inert gas stream is then cooled in an air cooler 25 followed by a water-cooled heat exchanger 26 so that condensable compounds, including the impurities desorbed from the bed 14, condense and separate from the inert gas. As a result a mixed gas/liquid phase stream exits the heat exchanger 26 and is fed by line 27 to a gas/liquid separator 28, where liquid component is removed and purged through line 29.

In order to maximize the removal of impurities in the gas/liquid separator 28, when the production of liquid in the separator 28 has diminished to near zero, a condensable fluid, such as water, is added to inert gas stream at one or more points between the pretreatment unit 13 and the gas/liquid separator 28. Suitable points are shown in FIG. 2 and include through line 31 upstream of the air cooler 25, through line 32 downstream of the air cooler 25 but upstream of the heat exchanger 26 and through line 33 downstream of the heat exchanger 26 but upstream of the gas/liquid separator 28.

After rejection of the condensed liquid component in the gas/liquid separator 28, the inert gas stream, a small portion of the inert gas stream, generally less than 20 volume % of the inert gas leaving the separator 28, is purged through line 34. The remainder of the inert gas stream is combined with make-up inert gas, introduced through line 35, and recycled to the compressor 21. Each reactivation cycle is continued until the adsorbent bed returns to between about 50 and about 90% of its initial adsorbent capacity, which typically takes from about 8 to about 72 hours.

Although the pretreatment unit shown in the drawings is intended for removing impurities from aromatic hydrocarbon feedstock to an aromatics alkylation process, a similar arrangement could be used for removing impurities from the olefin component of the feed.

In practice, an aromatic alkylation plant will typically have a plurality of pretreatment units arranged so that at least one pretreatment unit is always in adsorption mode while other pretreatment unit(s) are in reactivation mode, thereby allowing continuous purification of the benzene feed.

The invention will now be more particularly described with reference to the following Example.

EXAMPLE 1

A benzene feedstock is passed through a pretreatment unit containing a bed of 13× molecular sieve adsorbent operating at a temperature of 110° C. to reduce the nitrogenous impurities in the feedstock to less 0.05 ppm by weight. After 90 days on stream, the concentration of nitrogenous impurities exceeds the target value, and the adsorbent is deemed spent. The supply of benzene is ceased and, after draining liquid benzene from the pretreatment unit, a compressed and heated nitrogen stream is passed through the bed counter-current to the direction of flow for the adsorption cycle to increase the temperature of the bed to 260° C. and to desorb the nitrogenous impurities from the bed. The hot impurity-containing nitrogen stream leaving the bed is cooled first in an air cooler to a temperature of 65° C. and then to 15° C. in a chilled water-cooled heat exchanger so that condensable compounds condense and separate from the nitrogen. The resultant mixed nitrogen/liquid phase stream is then fed to a gas/liquid separator, where the liquid component is removed to leave a purified nitrogen stream, which is recycled to the pretreatment unit. The reactivation process is terminated after a period of 36 hours. A sample of the adsorbent is analyzed for residual nitrogenous impurity content.

In separate tests the above process is repeated but in one test a liquid water stream is added to the mixed nitrogen/liquid phase stream before the latter enters the gas/liquid separator. The reactivation process is terminated after 36 hours and the adsorbent is sampled and analyzed as described above. The addition of the water is found to decrease the amount of nitrogenous impurities retained by the adsorbent following reactivation by 50% as compared with the test without the water addition.

The invention claimed is:

1. A process for alkylating an aromatic hydrocarbon with an olefin, the process comprising:
   (a) passing a feedstock selected from the aromatic hydrocarbon and the olefin through a pretreatment unit containing an adsorbent such that the adsorbent removes impurities contained by the feedstock;
   (b) terminating passage of said feedstock through the pretreatment unit;
   (c) passing a heated inert gas through the pretreatment unit such that the inert gas desorbs impurities from the adsorbent to produce an inert gas effluent stream containing the desorbed impurities;
   (d) adding a condensable fluid to at least part of the inert gas effluent stream such that at least a portion of the impurities contained therein condense with said fluid to leave a purified inert gas stream;
   (e) recycling the purified inert gas stream to (c); and
   (f) reacting the aromatic hydrocarbon and the olefin in the presence of a zeolite alkylation catalyst after the pretreatment (a).

2. The process of claim 1, wherein the passing (a) is conducted at a first temperature and the inert gas is heated in (c) to a second temperature at least 50° C. higher than the first temperature.

3. The process of claim 2, wherein the feedstock is said aromatic hydrocarbon and said first temperature is from 100° C. to 170° C.

4. The process of claim 2, wherein the feedstock is said aromatic hydrocarbon and said first temperature is from 110° C. to 130° C.

5. The process of claim 2, wherein the feedstock is said olefin and said first temperature is from 20° C. to 100° C.

6. The process of claim 2, wherein the feedstock is said olefin and said first temperature is from 40° C. to 70° C.

7. The process of claim 1, wherein the inert gas comprises nitrogen.

8. The process of claim 1, wherein the condensable fluid is selected from ethylbenzene plant residue, cumene plant residue, ethylbenzene, cumene, benzene, water and mixtures thereof.

9. The process of claim 1, wherein the aromatic hydrocarbon feedstock comprises benzene and the olefin feedstock comprises ethylene or propylene.

10. The process of claim 1, wherein the impurities in said at least one feedstock are selected from inorganic or organic compounds containing nitrogen, sulfur, phosphorus, or oxygen atoms.

11. The process of claim 1, wherein the inert gas effluent stream is passed through a liquid-cooled chiller to a gas/liquid separator where said impurities are partially removed together with the condensed fluid.

12. The process of claim 11, wherein the condensable fluid is added to the inert gas effluent stream upstream of the chiller.

13. The process of claim 11, wherein the condensable fluid is added to the inert gas effluent stream downstream of the chiller but upstream of the gas/liquid separator.

* * * * *

UNITED STATES PATENT AND TRADEMARK OFFICE
CERTIFICATE OF CORRECTION

PATENT NO. : 10,280,128 B2
APPLICATION NO. : 14/416193
DATED : May 7, 2019
INVENTOR(S) : Brian Maerz et al.

Page 1 of 1

It is certified that error appears in the above-identified patent and that said Letters Patent is hereby corrected as shown below:

In the Specification

Column 4, Line 49 should read: "... stream exits the pretreatment unit 13 through line 24. The hot ..."

Signed and Sealed this
Thirtieth Day of July, 2019

Andrei Iancu
*Director of the United States Patent and Trademark Office*